(12) United States Patent
Malchow

(10) Patent No.: US 10,316,173 B2
(45) Date of Patent: Jun. 11, 2019

(54) SYSTEMS AND METHODS FOR MARKING PLASTICS

(71) Applicant: Sensors Unlimited, Inc., Princeton, NJ (US)

(72) Inventor: Douglas S. Malchow, Lawrence, NJ (US)

(73) Assignee: Sensors Unlimited, Inc., Princeton, NJ (US)

(*) Notice: Subject to any disclaimer, the term of this patent is extended or adjusted under 35 U.S.C. 154(b) by 440 days.

(21) Appl. No.: 15/012,501

(22) Filed: Feb. 1, 2016

(65) Prior Publication Data

US 2017/0219481 A1 Aug. 3, 2017

(51) Int. Cl.
| G01J 5/02 | (2006.01) |
| C08K 11/00 | (2006.01) |
| G01N 21/25 | (2006.01) |
| C08J 3/20 | (2006.01) |
| G01N 21/31 | (2006.01) |
| G01N 21/63 | (2006.01) |
| C08J 3/22 | (2006.01) |
| G01N 21/3563 | (2014.01) |
| G01N 21/64 | (2006.01) |

(52) U.S. Cl.
CPC ............ C08K 11/00 (2013.01); C08J 3/20 (2013.01); C08J 3/226 (2013.01); G01N 21/25 (2013.01); G01N 21/31 (2013.01); G01N 21/3563 (2013.01); G01N 21/63 (2013.01); G01N 21/643 (2013.01); C08J 2423/04 (2013.01); C08J 2425/04 (2013.01)

(58) Field of Classification Search
CPC .. C08K 11/00; G01N 21/3563; G01N 21/643; G01N 21/25; G01N 21/31; G01N 21/63; C08J 3/226; C08J 3/20; C08J 2423/04; C08J 2425/04
See application file for complete search history.

(56) References Cited

U.S. PATENT DOCUMENTS

| 5,201,921 A | 4/1993 | Luttermann et al. |
| 5,329,127 A | 7/1994 | Becker et al. |
| 5,397,819 A | 3/1995 | Krutak et al. |
| 5,794,788 A * | 8/1998 | Massen ................. B07C 5/126 209/524 |

(Continued)

FOREIGN PATENT DOCUMENTS

| DE | 4433937 A1 | 3/1996 |
| EP | 1300200 A1 | 4/2003 |

(Continued)

*Primary Examiner* — Kiho Kim
(74) *Attorney, Agent, or Firm* — Locke Lord LLP; Scott D. Wofsy; Georgi Korobanov

(57) ABSTRACT

A method of determining the composition of a polymeric body includes applying electromagnetic radiation to the polymeric body, modulating the electromagnetic radiation using a tagant disposed within a polymer composition forming the polymeric body, and receiving the modulated electromagnetic radiation from the tagant at an infrared detector. The electromagnetic radiation received from the tagant has a signature corresponding to the polymer composition forming the polymeric body. A method of making a polymeric body and system for determining composition of a polymeric body are also described.

10 Claims, 5 Drawing Sheets

(56) References Cited

U.S. PATENT DOCUMENTS

| | | | |
|---|---|---|---|
| 6,091,491 A | 7/2000 | Chisholm et al. | |
| 6,809,812 B2 | 10/2004 | Yin | |
| 2010/0200649 A1* | 8/2010 | Callegari | G06K 19/086 |
| | | | 235/375 |
| 2014/0367316 A1 | 12/2014 | Saeedkia | |

FOREIGN PATENT DOCUMENTS

| | | |
|---|---|---|
| GB | 2330409 A | 4/1999 |
| WO | WO-0044508 A2 | 8/2000 |
| WO | WO-2015036719 A1 | 3/2015 |

* cited by examiner

SYSTEMS AND METHODS FOR MARKING PLASTICS

BACKGROUND OF THE INVENTION

1. Field of the Invention

The present disclosure relates to plastics, and more particularly to marking plastics for optical identification.

2. Description of Related Art

Plastics have gained widespread acceptance and are commonly found in food packaging, consumer electronics, and automotive applications. One consequence of the widespread use of plastics is the need to dispose of plastic objects—ideally through a recycling process. Recycling can enable the material forming discarded plastic objects to be reused in the manufacture of new plastic objects, thereby reducing virgin material in such objects. One challenge to recycling plastics is that some plastic materials are incompatible with other plastic materials, like styrene and polyethylene, where relatively small amounts of the first material intermixed with the second material can render the aggregated materials unsuitable for reuse. Recycling processes therefore generally sort plastic objects by composition, typically using optical systems that determine the composition of the object based on the spectral response of the plastic material to light. While generally satisfactory, some plastic materials can resist traditional optical sorting techniques due the composition of the plastic object. Dark plastic materials, for example, tend to exhibit insufficient spectral response to the light used in traditional optical sorting.

Such conventional methods and systems of plastic sorting have generally been considered satisfactory for their intended purpose. However, significant amounts of plastics can remain unidentified at the end of traditional sorting processes, so there is still a need in the art for improved systems and methods for determining the composition of plastic objects. The present disclosure provides a solution for this need.

SUMMARY OF THE INVENTION

A method of determining the composition of a polymeric body includes applying electromagnetic radiation to the polymeric body, modulating the electromagnetic radiation using a tagant disposed within a polymer composition forming the polymeric body, and receiving the modulated electromagnetic radiation from the tagant at an infrared detector. The electromagnetic radiation received from the tagant has a signature corresponding to the polymer composition forming the polymeric body.

In certain embodiments, the method can include introducing the tagant into the polymer composition. The polymeric body can be formed from the tagant and the polymer composition. The tagant can be selected based on the polymer composition forming the polymeric body. The tagant can be selected from a group of tagants. Each tagant in the group of tagants can be associated with a chemically unique polymer composition. The tagant can include a nanoparticulate or a material with a nanocrystalline structure that modulates electromagnetic radiation differently than the polymer composition forming the polymeric body. The polymer composition of the polymeric body can be determined using the infrared signature in the reflected electromagnetic radiation. The infrared signature can reside within a wavelength band extending between about 500 nanometers and about 2500 nanometers. The infrared signature can reside within a wavelength band extending between about 700 nanometers and about 1700 nanometers. The infrared signature can reside within a wavelength band extending between about 900 nanometers and about 1700 nanometers. The infrared signature can reside within a wavelength band extending between about 950 nanometers and about 1700 nanometers. It is contemplated that the polymeric body can include a material that absorbs substantially all electromagnetic radiation applied to the polymer composition, such a carbon black or other dark pigmentation composition.

In accordance with certain embodiments, the nanoparticulate or nanocrystalline structure of the tagant can fluoresce in response to electromagnetic radiation incident on the polymeric body. The electromagnetic radiation applied to the polymeric body can include wavelengths outside of infrared portion of the electromagnetic spectrum. The electromagnetic radiation applied to the polymeric body can be broadband electromagnetic radiation. A portion of the electromagnetic radiation applied to the polymeric body can be received at a first wavelength, shifted to a second wavelength, and emitted by the tagant. The electromagnetic radiation emitted by the tagant can include an infrared signature corresponding to the polymer composition forming the polymeric body. The emitted electromagnetic radiation can be received at an infrared detector, and the polymer composition of the polymeric body determined using the infrared signature in the emitted electromagnetic radiation.

It is also contemplated that, in accordance with certain embodiments, the tagant can reflect electromagnetic radiation applied to the polymeric body. The tagant can selectively attenuate electromagnetic radiation applied to the polymeric body at a first wavelength more heavily than that of a second wavelength applied to the polymeric body. The electromagnetic radiation applied to the polymeric body can be infrared electromagnetic radiation. The electromagnetic radiation applied to the polymeric body can be narrowband electromagnetic radiation. The electromagnetic radiation reflected by the tagant can include an infrared signature. The infrared signature in the reflected electromagnetic radiation can be associated with the polymer composition forming the polymeric body. The reflected electromagnetic radiation can be received at an infrared detector, and the polymer composition of the polymeric body determined using the infrared signature in the emitted electromagnetic radiation.

A method of marking a polymeric body includes introducing a tagant into a polymer composition. A polymeric body can be formed using the tagant and polymer composition mixture. The tagant and polymer composition used to form the polymeric body can include a dark pigmentation composition.

A system for determining the polymer composition forming of a polymeric body includes an illuminator, an infrared sensor configured to optically couple with the illuminator through the infrared sensor, and a controller. The controller is operably connected to the illuminator and the infrared sensor, and includes a processor and a memory. The processor is communicative with the memory, and the memory has recorded on it a plurality of program modules with instructions that, when read by the processor, cause the processor to execute the steps of the above-described method.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION OF THE PREFERRED EMBODIMENTS

Figure 1:
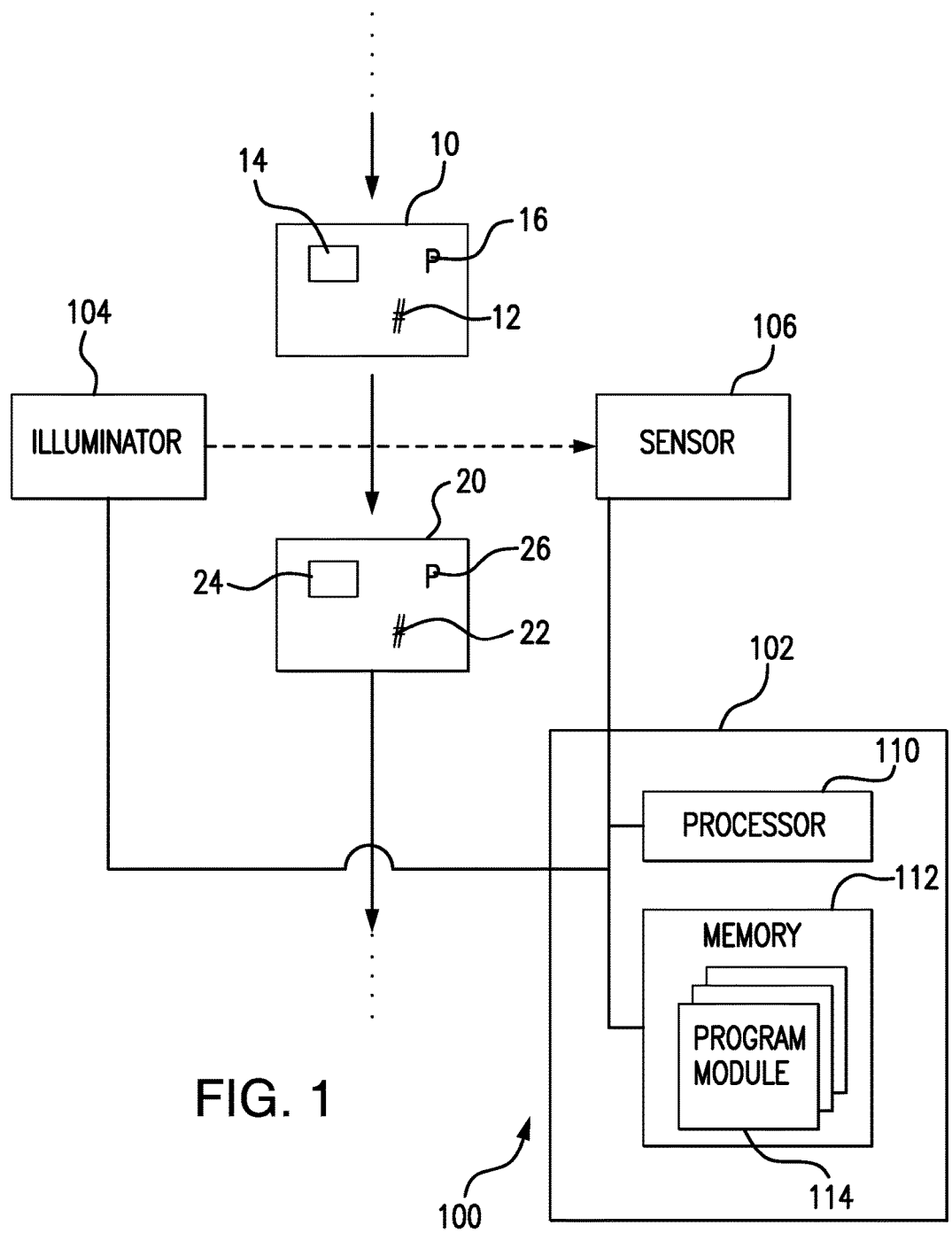
FIG. 1 is a schematic view of an exemplary embodiment of a system for determining composition of a polymeric body, showing the system applying electromagnetic radiation to polymeric bodies having tagants.

Reference will now be made to the drawings wherein like reference numerals identify similar structural features or aspects of the subject disclosure. For purposes of explanation and illustration, and not limitation, a partial view of an exemplary embodiment of a system for determining the polymer composition of a polymeric body is shown in FIG. 1 and is designated generally by reference character 100. Other embodiments of systems and methods for determining the polymer composition of polymeric bodies are shown in FIGS. 2-5, as will be described. The systems and methods described herein can be used for determining the polymer composition of polymeric bodies in a plastic recycling process; however the present disclosure is not limited to recycling or to plastics generally. For example, it is contemplated that the systems and methods described herein can also be used for the authentication of pharmaceutical products.

Referring to FIG. 1, system 100 is shown. System 100 includes a controller 102, an illuminator 104, and a sensor 106. In embodiments, illuminator 104 includes a broadband illuminator source, such as an incandescent or light-emitting diode. The broadband illuminator source can be configured and adapted to apply electromagnetic radiation to a polymeric body of interest, including wavelengths within the infrared portion of the electromagnetic spectrum. In certain embodiments, illuminator 104 includes a narrowband illuminator source, such as a laser. The narrowband illuminator source can be configured and adapted to the polymeric body of interest, including wavelengths outside the infrared portion of the electromagnetic spectrum. Sensor 106 includes an infrared sensor. The infrared sensor includes a linear array that responds to electromagnetic radiation within a range between about 700 nanometers and about 2600 nanometers. In certain embodiments the infrared sensor respond to electromagnetic radiation with wavelengths between about 700 nanometers and 1450 nanometers, between about 700 nanometers and 1700 nanometers, between about 1100 nanometers and 2200 nanometers, or between about 1100 nanometers and about 2600 nanometers. It is contemplated that sensor 106 can include an infrared sensor response to electromagnetic radiation in the VIS-SWIR range, i.e. wavelengths between about 500 and 1700 nanometer, the NIR-SWIR range, i.e. wavelengths between about 700 and 1700 nanometers, or in the range of about 950 to about 1700 nanometers, reducing costs of sensor 106. Examples of suitable infrared sensors include infrared sensors marketed under the tradename Sensors Unlimited, available from UTC Aerospace Systems of Charlotte, N.C.

Controller 102 includes a processor 110 and a memory 112. Processor 110 is operably connected to illuminator 104 and sensor 106, and is communicative with memory 112. Memory 112 has a plurality of program modules 114 recorded thereon that, when read by processor 110, cause processor 110 to execute certain operations. In this respect the instruction recorded in the plurality of program modules 114 of memory 112 cause processor 110 to apply electromagnetic radiation (indicated with dashed arrow) to the polymeric body of interest using illuminator 104. The instructions recorded in the plurality of program modules 114 of memory 112 also cause processor 110 to receive modulated electromagnetic radiation from the body of interest at sensor 106. The modulated electromagnetic radiation includes an infrared signature (shown in FIGS. 2 and 3) corresponding to a polymer composition forming the polymer body of interest. The instructions recorded in the plurality of program modules 114 on memory 112 also cause processor 110 compare the infrared signature with a plurality of infrared signatures stored in the plurality of program modules 114 on memory 112. Based on the comparison, processor 110 determines the polymer composition of the polymeric body using the association of the polymer composition forming the polymeric body of interest with the infrared signature in the electromagnetic radiation received by sensor 106.

With continuing reference to FIG. 1, system 100 is configured to optically couple illuminator 104 with sensor 106 through one or more polymeric bodies of interest. In this respect, a first polymeric body 10 and a second polymeric body 20 are provided to system 100 for polymer composition determination.

First polymeric body 10 includes a first polymer composition 12 with a first tagant 14 disposed within first polymer composition 12. First tagant 14 is associated with first polymer composition 12, and may include a nanoparticulate material or a nanocrystalline material structure distributed within first polymeric body 10. Optionally, a dark pigmentation composition 16 can also be disposed first polymeric body 10, such as carbon black by way of non-limiting example.

Second polymeric body 20 is similar to first polymeric body 10 with the differences that (a) second polymer composition 22 has a different chemical makeup than first polymer composition 12, and (b) second tagant 24 has a response to electromagnetic radiation incident to second polymer composition 22 that is different than the response to the electromagnetic radiation incident to first polymer composition 12. The distinct responses of the tagant are discernable by sensor 106 and are associated with chemical makeup of the respective polymer composition in the one or more plurality of program modules 110 recorded on member 112. It is contemplated that first polymer composition 12 may be of a type that is incompatible with second polymer composition 22, e.g., one is a styrene-type composition while the other is polyethylene-type composition. It is to be appreciated that this is for purposes of illustration purposes only and non-limiting, and that the systems and methods described herein can be used with any type of polymer composition.

Figure 2:
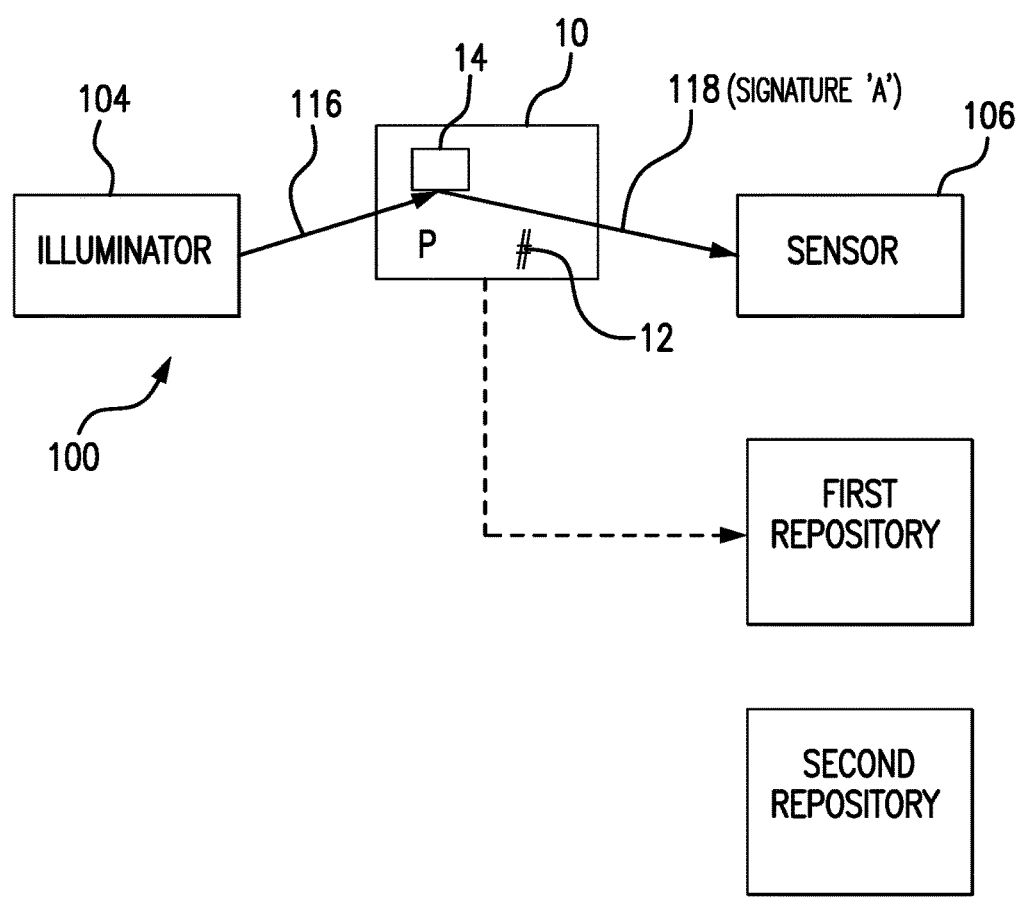
FIG. 2 is a schematic view of the system of FIG. 1, showing a polymeric body selectively attenuating and reflecting infrared electromagnetic radiation applied to the polymeric body.

With reference to FIG. 2, first polymeric body 10 is shown. First tagant 14 is distributed within first polymeric body 10 and includes a material that attenuates certain infrared wavelength more heavily than other infrared wavelengths. It is contemplated that first tagant may include a material with a nanocrystalline structure that selectively attenuates electromagnetic radiation of certain wavelengths more heavily than electromagnetic radiation of other infrared wavelengths. Selective attenuation of one or more predetermined infrared wavelengths encodes infrared electromagnetic radiation reflected from first tagant 14 with signature 'A', which is discernable to sensor 106, and which is associated with first polymer composition 12 in memory 112 (shown in FIG. 1).

Illuminator 104 applies electromagnetic radiation 116 to first polymeric body 10. It is contemplated that electromagnetic radiation 116 includes broadband electromagnetic radiation. In certain embodiments electromagnetic radiation 116 may include relatively low-energy electromagnetic radiation. Electromagnetic radiation 116 may be provided by a light-emitting diode or an incandescent source incorporated in illuminator 104. It is contemplated that electromagnetic radiation 116 includes wavelengths within the infrared portion of the electromagnetic spectrum.

First tagant 14 modulates the applied electromagnetic radiation 116 by selectively attenuating one or more of the infrared wavelengths within electromagnetic radiation 116. In this respect the selectively attenuated wavelength(s) of electromagnetic radiation form a signature within reflected electromagnetic radiation 118 that is discernable to sensor 106.

Sensor 106 receives reflected electromagnetic radiation 118 bearing the signature imparted by first tagant 14, and provides the signature to controller 110 (shown in FIG. 1). Processor 110 compares the signature received from sensor 106 to signatures resident in memory 112 and determines, through an association of the signature with a chemically unique polymer composition, the constitution of composition first polymeric composition 12. Based on the determination of the constitution of first polymeric composition 12, system 100 routes first polymeric body 10 to a selected repository, as shown with the dashed arrow in FIG. 2, which in the illustrated exemplary example is a first repository designated for styrene-containing polymeric bodies.

Figure 3:
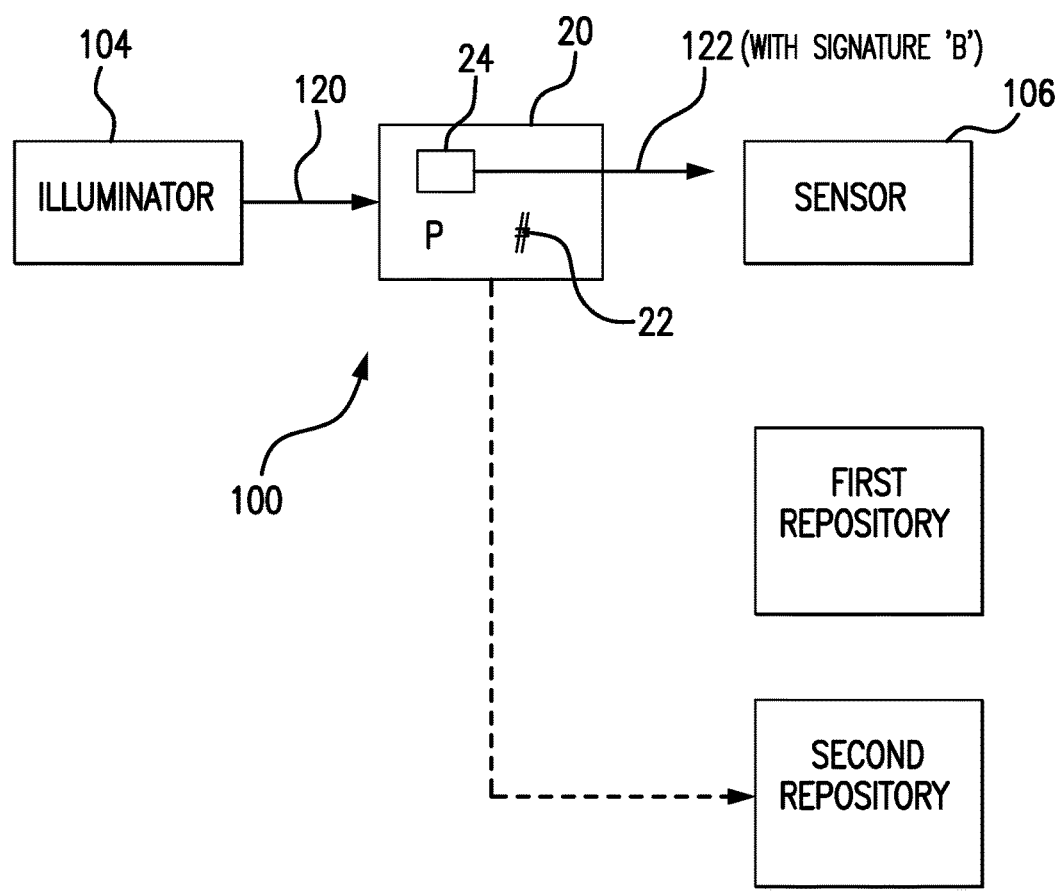
FIG. 3 is a schematic view of the system of FIG. 1, showing a polymeric body emitting electromagnetic radiation having an infrared wavelength.

With reference to FIG. 3, second polymeric body 20 is shown. Second tagant is distributed within second polymeric body 20 and includes a material that fluoresces when exposed to electromagnetic radiation of certain wavelengths. It is contemplated that second tagant 24 include a nanoparticulate that, upon receipt of electromagnetic radiation, emits electromagnetic radiation of a wavelength differing from that incident upon the nanoparticulate. In this respect electromagnetic radiation incident on the nanoparticulate provokes fluorescence from second tagant 24. Fluorescence of second tagant 24 encodes electromagnetic radiation emitted by second tagant 24 with signature 'B', which is discernable to sensor 106, and which is further associated with second polymer composition 22 in memory 112 (shown in FIG. 1).

Illuminator 104 applies electromagnetic radiation 120 to second polymeric body 20. It is contemplated that electromagnetic radiation 120 includes narrowband electromagnetic radiation. In certain embodiments electromagnetic radiation 120 may include relatively high-energy electromagnetic radiation. Electromagnetic radiation 120 may be provided by a laser source incorporated in illuminator 104.

It is contemplated that the electromagnetic radiation 120 may include wavelengths outside of the infrared portion of the electromagnetic spectrum.

Responsive to electromagnetic radiation 120, second tagant 24 emits electromagnetic radiation 122. The emitted electromagnetic radiation 122 includes an infrared wavelength and is encoded with a signature 'B'. Signature 'B' is associated with second polymer composition 22, and is cognizable to sensor 106.

Sensor 106 receives the emitted electromagnetic radiation 120 bearing the signature imparted by second tagant 24 and provides the signature to controller 102 (shown in FIG. 1). Using processor 110 (shown in FIG. 1), controller 102 compares the signature received from sensor 106 to signatures resident in memory 112 (shown in FIG. 1) and determines, through an association of signature 'B' with second polymer composition 22 resident on member 112, constitution of second polymeric body 12. Based on the determined constitution, system 100 routes second polymeric body 20 to repository designated for second polymer composition 22, as shown with the dashed arrow in FIG. 3. In the illustrated exemplary example the second repository is designated for polymeric bodies formed from polyethylene.

Figure 4:
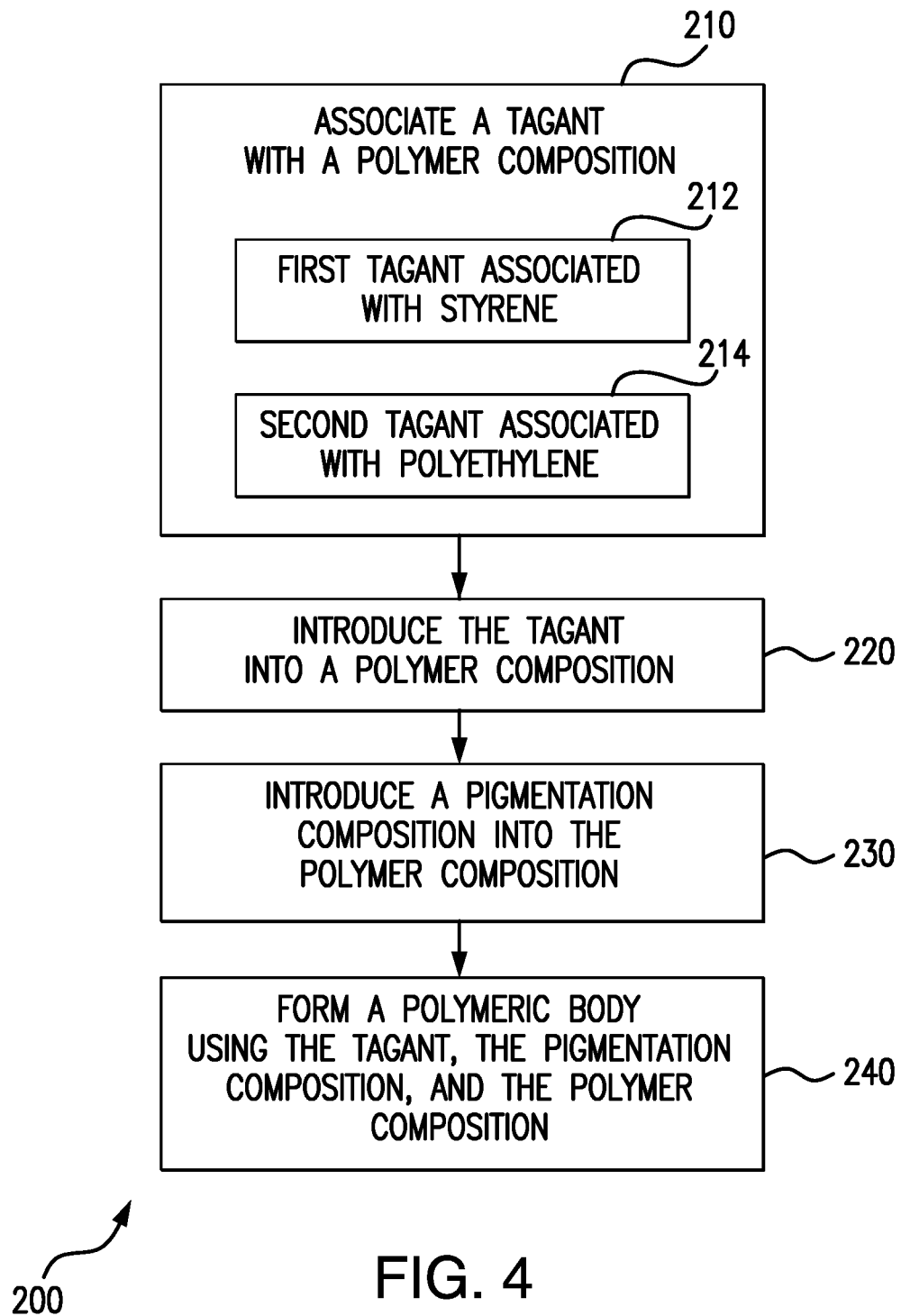
FIG. 4 is a process flow diagram of a method of marking a polymeric body, showing steps for marking a polymeric body by introducing a tagant into a polymer composition of the polymeric body.

With reference to FIG. 4, a method 200 of marking a polymeric body, e.g., first polymeric body 10 or second polymeric body 20 (shown in FIG. 1). Method 200 includes associating a tagant with a polymer composition, as shown with box 210. For example, first tagant 14 (shown in FIG. 1) can be associated with first polymer composition 12 (shown in FIG. 1), as shown with box 212. First tagant may be a styrene-containing polymer composition. Second tagant 24 (shown in FIG. 1) can be associated with second polymer composition 22 (shown in FIG. 1), as shown with box 214. Second polymer composition 22 can be a polyethylene-containing polymer composition. The tagant can be introduced into the associated polymer composition, as shown with box 220, and a polymeric body including the tagant and associated polymer composition can be formed, as shown with box 240. Optionally, a dark pigmentation composition, e.g., pigmentation composition P (shown in FIG. 1), can also be introduced into the tagant/polymer composition, as shown with box 230.

Figure 5:
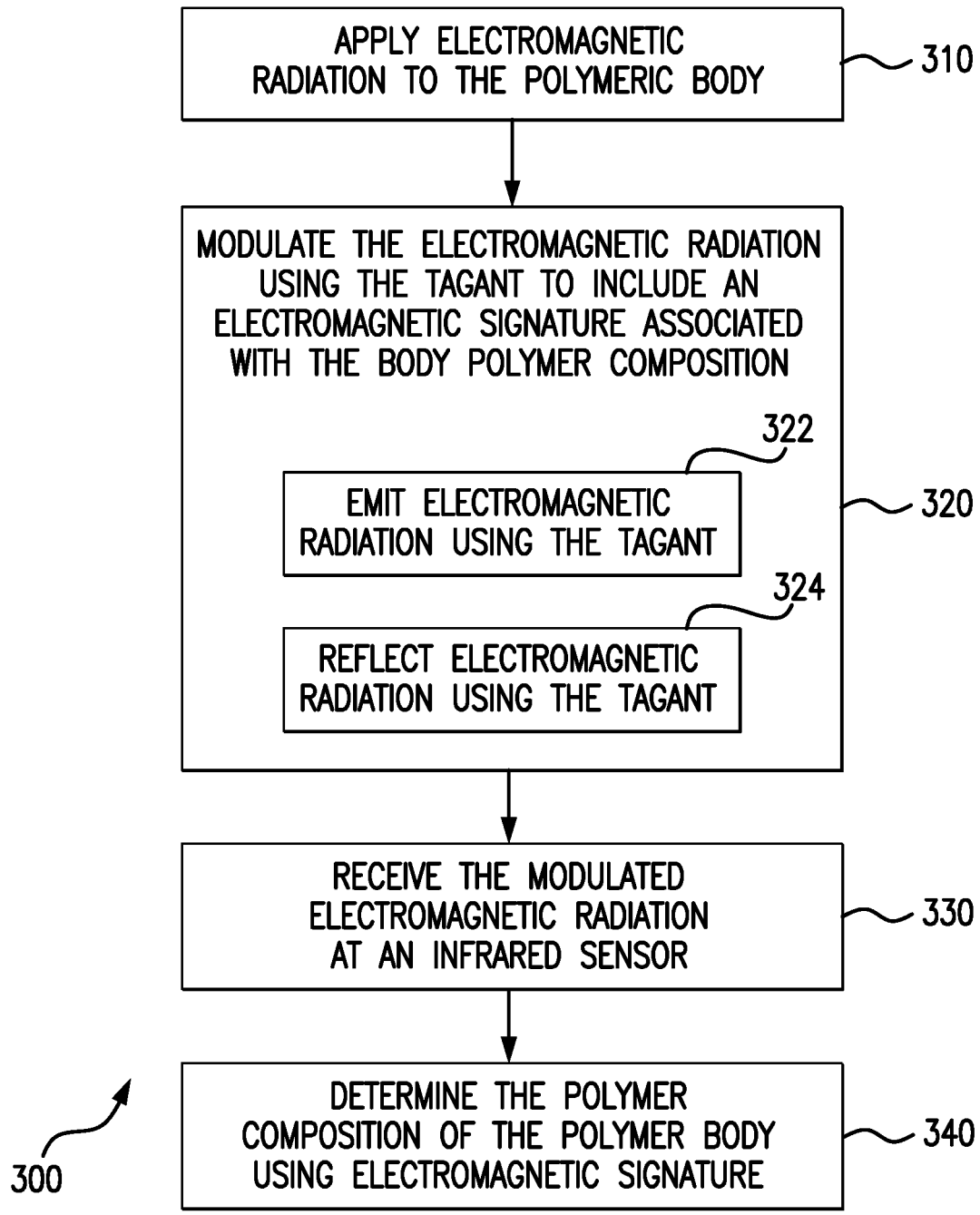
FIG. 5 is a process flow diagram of a method of determining the polymer composition forming a polymeric body, showing steps for modulating electromagnetic radiation applied to the polymeric body to include a spectral signature corresponding to the polymer composition forming the polymeric body.

With reference to FIG. 5, a method 300 of determining constitution of a polymeric body is shown. Method 300 generally includes applying electromagnetic radiation to a polymeric body, as shown with box 310, modulating the electromagnetic radiation to include a signature associated with a polymer composition of the polymeric body, as shown with box 320, and receiving the electromagnetic radiation at an infrared sensor, as shown with box 33. Based on the signature in the modulated electromagnetic radiation received by the infrared sensor, a determination is made regarding the polymer composition of the polymeric body based on the signature, as shown with box 340.

Dark or black plastic materials can be difficult to classify in conventional sorting techniques due to the carbon black commonly included in such materials for pigmentation. Because the carbon black typically absorbs a significant portion of light applied to the material by traditional optical sorting systems, such materials may be difficult to quickly and cheaply sort based on the plastic material resin-type.

In embodiments described herein, plastic objects include tagants. The tagants selected to be relatively inert, with little influence on the properties of the polymer composition forming the plastic object, and have a spectral signature assigned to identify a polymer composition included in a specific plastic object. The spectral signature of the tagant is discernable by an infrared sensor upon application of electromagnetic radiation to the plastic body, either through infrared radiation emitted by the tagant or by infrared wavelengths of the applied electromagnetic radiation selectively attenuated by the tagant.

In certain embodiments described herein, the spectral signature of the tagant is associated with the polymer composition forming the plastic object in a memory of a sorting system. In certain embodiments, the sorting system applied electromagnetic radiation to the plastic body, the tagant modulates the applied electromagnetic radiation, and an infrared sensor receives the modulated electromagnetic radiation including the spectral signature. Based upon the spectral signature the plastic body routed to a repository designated for polymer compositions of the constitution associated with the spectral signature. It is contemplated that the spectral signature be used to segregate from one another polymer compositions that are incompatible with one another in a reuse setting, for example, styrene-containing and polyethylene-containing plastic materials.

The methods and systems of the present disclosure, as described above and shown in the drawings, provide for sorting systems with superior properties including the capability to discern the identity of plastic objects despite very-low reflectivity when irradiated with electromagnetic radiation in the visible portion of the electromagnetic spectrum, the near-infrared portion of the electromagnetic spectrum, and/or the shortwave infrared portion of the electromagnetic spectrum. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A method for determining the composition of a polymeric body, comprising:
    applying electromagnetic radiation to a polymeric body, wherein the polymeric body includes carbon black;
    modulating the electromagnetic radiation using a tagant disposed within the polymeric body, wherein modulating the electromagnetic radiation comprises reflecting the electromagnetic radiation using the tagant,
    wherein the tagant reflects a greater portion of the electromagnetic radiation of a first wavelength than electromagnetic radiation of a second wavelength; and
    receiving the modulated electromagnetic radiation at an infrared detector, wherein the modulated electromagnetic radiation includes an infrared signature corresponding to a polymer composition forming the polymeric body.

2. A method as recited in claim 1, further including associating the tagant with the polymer composition.

3. A method as recited in claim 2, wherein the tagant is associated with styrene or polyethylene.

4. A method as recited in claim 2, wherein the tagant includes a nanoparticulate material or a material with a nanocrystalline structure that selectively attenuates the applied electromagnetic radiation according to wavelength or fluoresces in response to the electromagnetic radiation.

5. A method as recited in claim 1, further including selecting the tagant based on a composition of the polymer composition forming the polymeric body.

6. A method as recited in claim 1, wherein the applied electromagnetic radiation is infrared electromagnetic radiation.

7. A method as recited in claim 1, wherein the applied electromagnetic radiation is broadband electromagnetic radiation.

8. A method as recited in claim 1, wherein the applied electromagnetic radiation is narrowband electromagnetic radiation.

9. A method as recited in claim 1, wherein modulating the electromagnetic radiation comprises emitting electromagnetic radiation having a wavelength that is different than the wavelength of electromagnetic radiation incident on the polymeric body.

10. A method as recited in claim 1, wherein modulating the electromagnetic radiation includes shifting the electromagnetic radiation from a first wavelength to a second wavelength.

* * * * *